US00PP29755P2

(12) United States Plant Patent
Deroose

(10) Patent No.: US PP29,755 P2
(45) Date of Patent: Oct. 16, 2018

(54) ***TILLANDSIA* PLANT NAMED 'T1072'**

(50) Latin Name: ***Tillandsia cyanea* Linden ex K. Koch.**
Varietal Denomination: T1072

(71) Applicant: Reginald Deroose, Evergem (BE)

(72) Inventor: Reginald Deroose, Evergem (BE)

( * ) Notice: Subject to any disclaimer, the term of this patent is extended or adjusted under 35 U.S.C. 154(b) by 0 days.

(21) Appl. No.: 15/731,385

(22) Filed: Jun. 5, 2017

(51) Int. Cl.
*A01H 5/02* (2018.01)

(52) U.S. Cl.
USPC ..... Plt./370

(58) Field of Classification Search
USPC ..... Plt./370
See application file for complete search history.

*Primary Examiner* — Keith O. Robinson
(74) *Attorney, Agent, or Firm* — Samuel R. McCoy, Jr.

(57) ABSTRACT

A new and distinct *Tillandsia* cultivar named 'T1072' which is characterized by a small, compact plant size that gives rise to a relatively large terminal rhipidium inflorescence with vibrant red-purple conduplicate bracts and violet flowers, as well as the stability of these characteristics from generation to generation.

4 Drawing Sheets

Latin name of the genus and species: The Latin name of the genus and species of the novel variety disclosed herein is *Tillandsia cyanea* Linden ex K. Koch.

Variety denomination: The inventive variety of *Tillandsia* disclosed herein has been given the variety denomination 'T1072'.

BACKGROUND OF THE INVENTION

Parentage: The *Tillandsia* variety 'T1072' is the result of a planned breeding program. The new variety originated as a seedling from the crossing of an unnamed proprietary *Tillandsia cyanea* plant (unpatented), the seed parent, with a second unnamed proprietary *Tillandsia cyanea* plant (unpatented) as the pollen parent. The crossing was made by the inventor at his greenhouse in Evergrem, Belgium in October of 1999. After observing the progeny of said cross, the new variety was selected in October of 2001 at the inventor's greenhouse in Evergrem, Belgium.

Asexual Reproduction: Asexual reproduction of the new cultivar 'T1072', by way of mericloning, was first initiated in November of 2001 at a tissue culture laboratory in Evergem, Belgium. Through five subsequent generations, the unique features of this cultivar have proven to be stable and true to type.

SUMMARY OF THE INVENTION

The cultivar 'T1072' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'T1072'. These characteristics in combination distinguish 'T1072' as a new and distinct *Tillandsia* cultivar:

1. *Tillandsia* 'T1072' exhibits a small, compact plant size; and
2. *Tillandsia* 'T1072' exhibits a large inflorescence relative to the small plant size; and 3. *Tillandsia* 'T1072' exhibits a terminal rhipidium inflorescence with vibrant red-purple conduplicate bracts and violet flowers.

BOTANICAL DESCRIPTION OF THE PLANT

Figure 1:
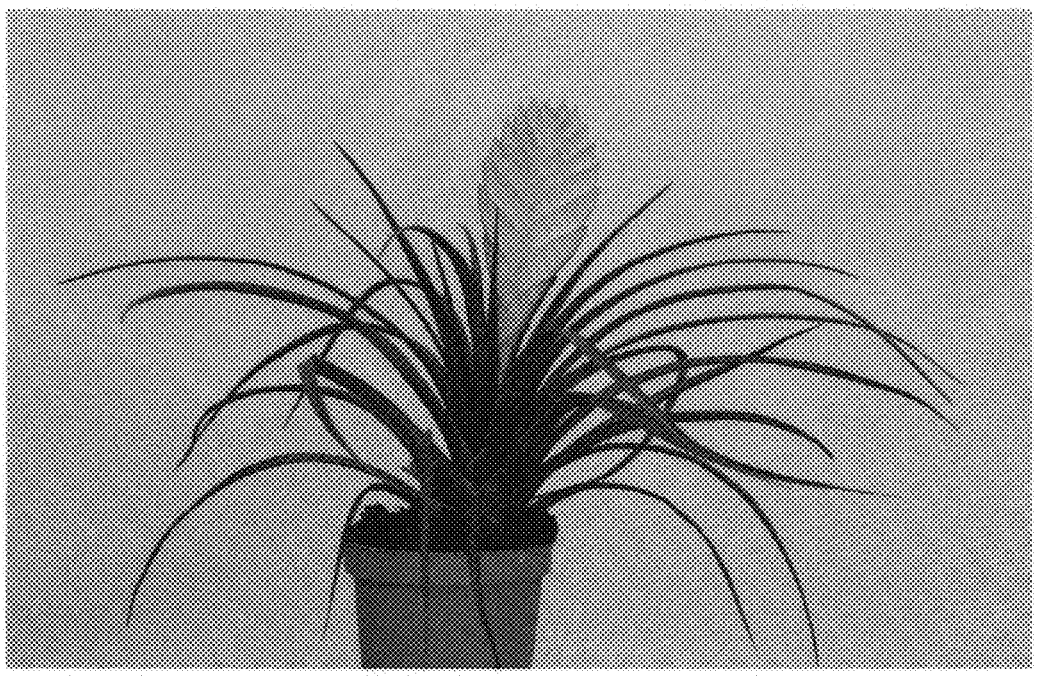
FIG. 1 illustrates, as nearly true as it is reasonably possible to make the same in color photographs of this type, an exemplary plant of 'T1072' grown in a commercial greenhouse in Evergrem, Belgium. This plant is approximately 12 months old from the time of mericloning, shown planted in a 9 cm nursery container.
Figure 2:
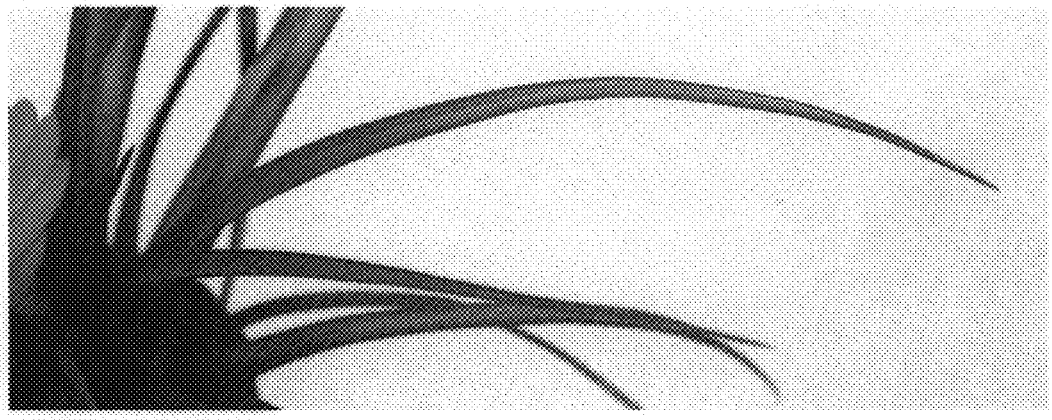
FIG. 2 illustrates, as nearly true as it is reasonably possible to make the same in color photographs of this type, the typical foliage of 'T1072'.
Figure 3:
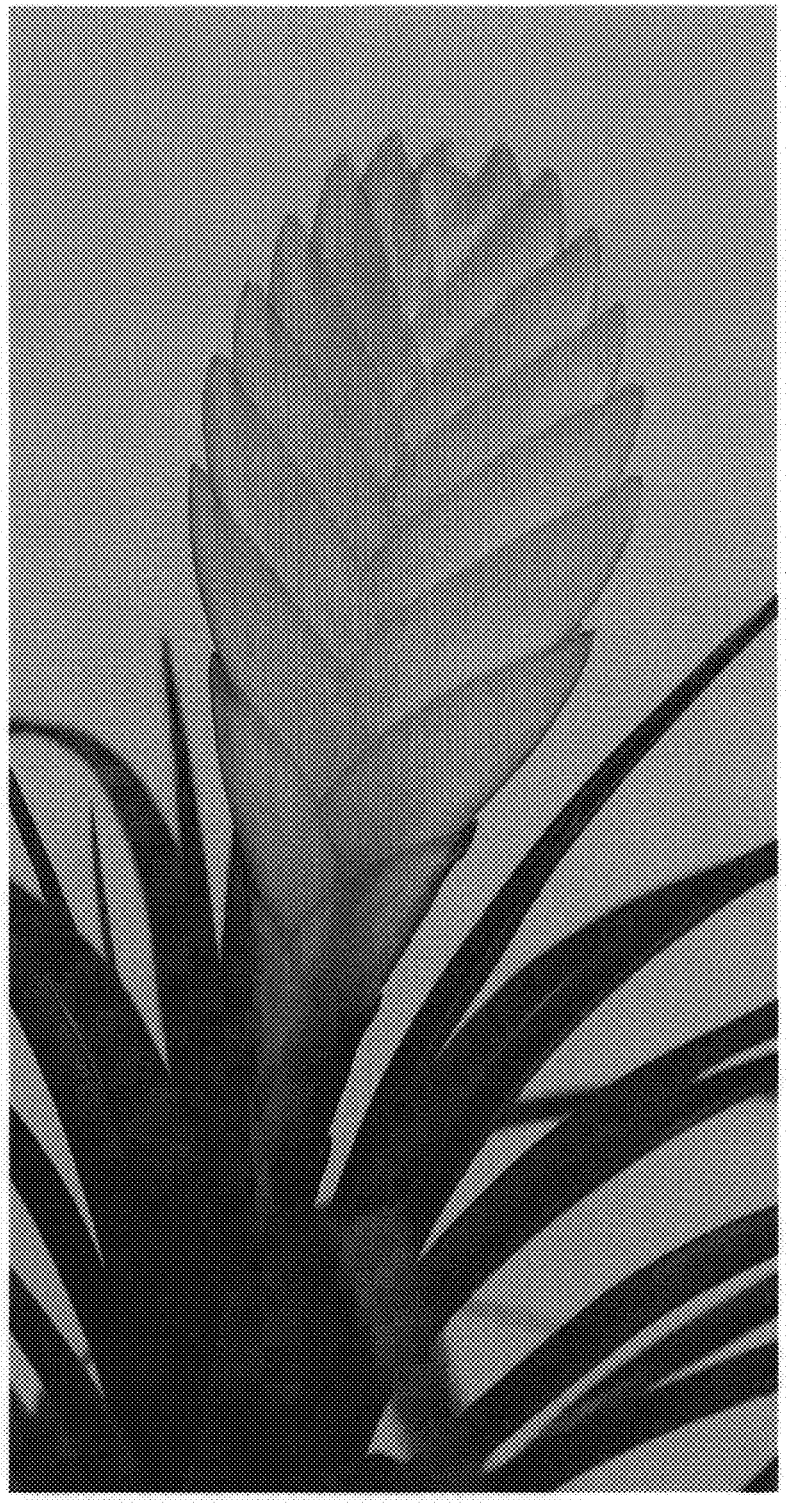
FIG. 3 illustrates, as nearly true as it is reasonably possible to make the same in color photographs of this type, the typical inflorescence of 'T1072'.
Figure 4:
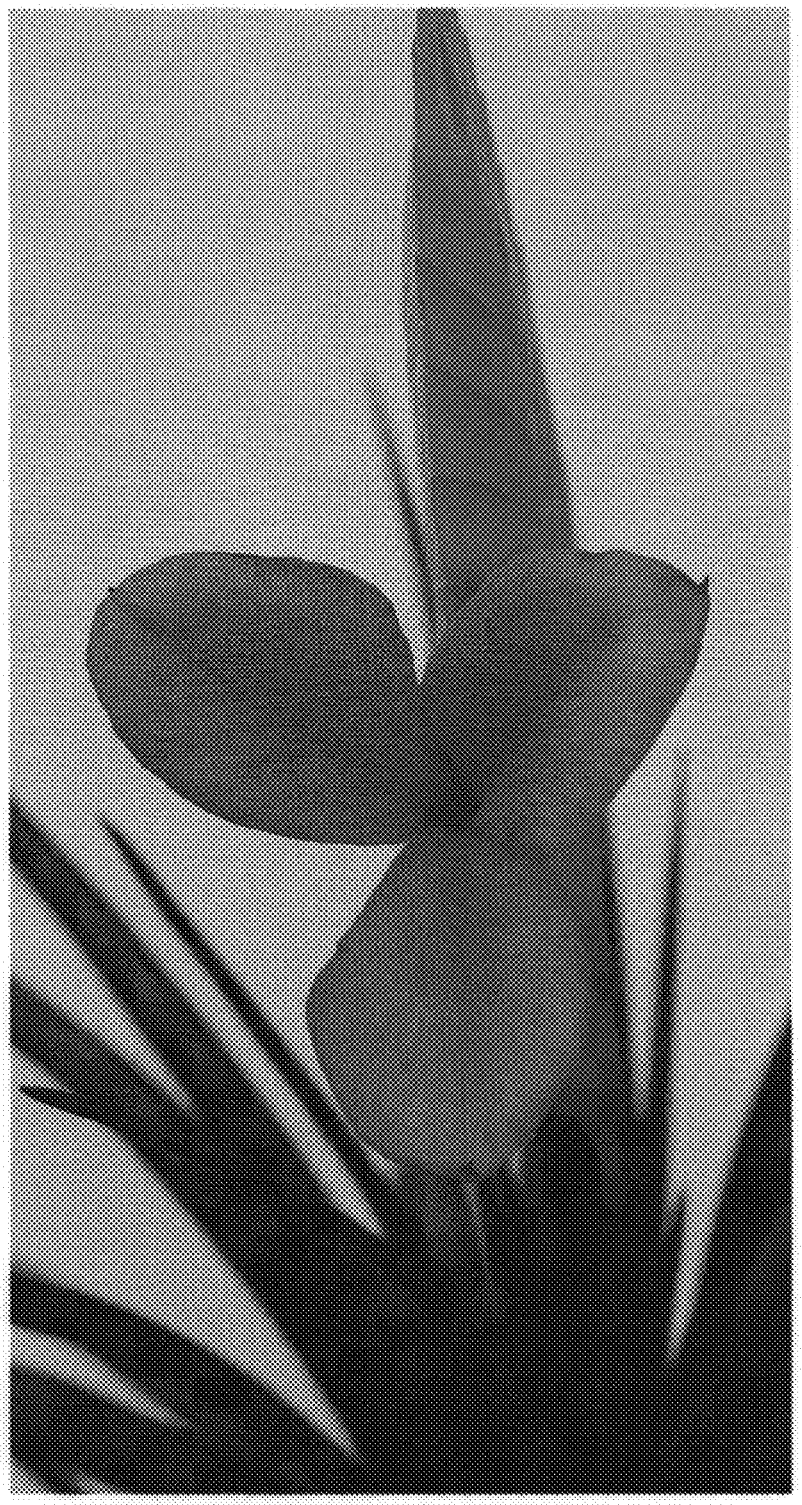
FIG. 4 illustrates, as nearly true as it is reasonably possible to make the same in color photographs of this type, the typical flower of 'T1072'.

The following observations and measurements made in April of 2017 describe averages from a sample set of six specimens of 12 month-old 'T1072' plants grown in 9 cm nursery pots at a greenhouse in Evergrem, Belgium. Plants were produced using conventional greenhouse production protocols for *Tillandsia* which consisted of regular overhead irrigation and fertigation applications. No pest or disease control measures were utilized in production. Plants were grown under shade (approximately 10,000 lux maximum) and no photoperiodic treatments or artificial light was given to the plants.

Those skilled in the art will appreciate that certain characteristics will vary with older or, conversely, with younger plants. 'T1072' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'T1072' and comparisons with the parents and most similar commercial variety of *Tillandsia* are provided below.

Plant description:

*Growth habit*.—Perennial; single monopodial basal rosette with inflorescences growing from the center of the rosette; a terminal inflorescence is carried above the leaf plane.

*Plant form*.—Flattened globular.

*Average height from base to top of foliar plane*.—15.8 cm.

*Average height from base to top of floral plane*.—18.6 cm.

*Plant spread*.—Average of 37.9 cm.

*Growth rate*.—Moderate.

*Plant vigor*.—Moderate.

*Propagation type*.—Mericloning.

*Time to initiate roots*.—About 14 days at approximately 20 degrees Celsius.

*Time to produce a marketable plant*.—Approximately 1 year in a 9 cm pot.

*Disease and pest resistance or susceptibility*.—Neither resistance nor susceptibility to typical *Tillandsia* pests and diseases has been observed.

*Environmental tolerances*.—Adapt to, at least, USDA Zones 10 and 12 and temperatures as high as 40 degrees Celsius; high tolerance to rain; high tolerance to wind.

Root system:

*General*.—Moderately dense rooting; roots are strong.

*Dimensions, mature roots*.—16.5 cm long with a diameter of 0.1 cm, on average.

*Texture*.—Fibrous, non-fleshy.

*Color*.—Brown, nearest RHS N200B.

Stem:

*Branching habit*.—Monopodial; no lateral branches present.

*Number of primary stems per plant*.—None; leaves form a basal rosette.

*Number of secondary branches per plant*.—None.

Foliage:

*Arrangement*.—Rosulate.

*Dimensions*.—23.9 cm long and 0.9 cm wide, on average.

*Shape of blade*.—Ligulate.

*Aspect*.—Involute.

*Attitude*.—Leaf base and proximal portion is at an average angle of 50 degrees to horizontal, with apex and distal most portion of the leaf at an approximate angle of minus 50 degrees to horizontal.

*Apex*.—Long, narrow acuminate.

*Base*.—Sheathing.

*Sheath dimensions*.—4.2 cm long and 2.5 cm wide, on average.

*Sheath color*.—Upper surface — Brown, nearest to RHS 200A, and fading to yellow-green towards the base, nearest to RHS 152D. Lower surface — Brown, nearest to RHS 200A but darker, and fading to yellow-green towards the base, nearest to RHS 152D.

*Margin*.—Entire.

*Pubescence, texture and luster of adaxial surface*.—Glabrous, smooth, and moderately glossy.

*Pubescence, texture and luster of abaxial surface*.—Glabrous, smooth, and slightly glossy.

*Color*.—Juvenile foliage, adaxial surface — Green, near RHS 137B, and fading to greyed-purple towards the base, nearest to RHS 187A. Juvenile foliage, abaxial surface — Green, near RHS NN137B, and fading to greyed-purple towards the base, nearest to RHS 187A. Mature foliage, adaxial surface — Green, nearest to RHS NN137B, and fading to greyed-purple towards the base, nearest to RHS 187A. Mature foliage, abaxial surface — Green, nearest to RHS 137A, and fading to a combination of greyed-purple and brown towards the base, nearest to in between RHS N186C and 200A.

*Venation*.—Parallel.

*Venation color, adaxial surface*.—Green, nearest to in between RHS NN137B and NN137C, and fading to greyed-purple towards the base, nearest to RHS 187A.

*Venation color, abaxial surface*.—Green, nearest to RHS 137A, and fading to a combination of greyed-purple and brown towards the base, nearest to in between RHS N186C and 200A.

*Petiole*.—No petioles present, leaves are sessile.

Inflorescence:

*Inflorescence arrangement*.—Terminal rhipidium, with prominent overlapping bracts.

*Natural flowering season*.—Late spring into winter in Evergrem, Belgium.

*Flowers per inflorescence*.—Approximately 15 unopened buds and 1 open flower.

*Height*.—10.6 cm.

*Diameter*.—Inflorescence is flattened, average width at widest point is 9.1 cm; average width at the narrowest point is 4.9 cm.

*Peduncle*.—Cross section — Ovate. Dimensions — Approximately 16.3 cm long and 0.6 cm wide at the narrowest point and 0.7 cm wide, at its widest. Aspect — Approximately 85 degree angle to horizontal. Strength — Strong. Texture and luster — Glabrous and glossy. Color — Yellow-green, nearest to RHS 145A.

Bud:

*Length*.—Average of 4.1 cm.

*Diameter*.—Average of 0.35 cm.

*Shape*.—Lanceolate.

*Pubescence, texture and luster*.—Glabrous, smooth and slightly glossy; moderately glossy at the base.

*Color*.—Red-purple, nearest to RHS 63A; lower half fading to yellow-green towards the base, nearest to RHS 145B.

Flower:

*Flower type*.—Complete; perfect.

*Flowering habit*.—Moderately floriferous.

*Shape*.—Salverform, with a single whorl of petals.

*Aspect*.—Flowers are outward to upward facing.

*Attachment*.—Sessile.

*Vertical height*.—5.1 cm.

*Corolla diameter.*—4.9 cm.

*Depth.*—*Approximately* 8.0 cm.

*Fragrance.*—Very light sweet, pleasant fragrance.

*Lastingness.*—Approximately 5 days.

*Persistent.*—Persistent.

*Corolla tube.*—Length — 4.8 cm. Diameter diameter — 0.35 cm. Texture — Smooth, glabrous. Color — White, nearest to RHS N155A. Venation color — White, nearest to RHS N155A.

*Throat of the corolla tube.*—Diameter — 0.3 cm. Texture — Smooth, glabrous. Color — Violet, nearest to in between RHS N87A and N88A. Venation color — Purple-violet, nearest to RHS N81A.

*Petals.*—Quantity of petals — 3. Connation — Sympetalous; proximal half of petals are fused. Arrangement — Rotate. Length — Approximately 8.6 cm. Width — Approximately 2.3 cm. Shape — Spatulate. Apex — Bluntly acute. Base — Fused. Margin — Irregular; no undulation. Pubescence, texture and luster of upper surface — Glabrous, moderately velvety and matte. Pubescence, texture and luster of lower surface — Glabrous, moderately velvety and matte. Color when opening, upper surface — Violet, nearest to in between RHS N87A and N88A. Color when opening, lower surface — Violet, in between RHS N87A and N88B but nearest to RHS N87A. Color when fully opened, upper surface — Purple-violet, nearest to RHS N81A. Color when fully opened, lower surface — Violet, nearest to RHS N87A. Fading, upper surface — Not fading. Fading, lower surface — Not fading. Venation color, fully opened, upper surface — White, near RHS NN155D; base is slightly tinged purple, near RHS N78C to N78D; apex is greyed-purple, near RHS N186C; entire petal is irregularly dotted red-purple, RHS 71A. Venation color, fully opened, lower surface — Purple-violet, near RHS N78C to N78D.

*Spurs.*—None.

*Calyx.*—Shape — Rotate. Length — 4.2 cm. Diameter — 0.7 cm. Sepals — Arrangement — Rotate; single whorl. Connation — Aposepalous. Quantity — 3. Length — 4.2 cm. Width — 0.3 cm. Shape — Linear. Apex — Narrow acute. Base — Broad cuneate. Margin — Entire. Texture and luster, upper surface — Smooth, glabrous, and moderately glossy. Texture and luster, lower surface — Smooth, glabrous, and matte. Color when opening, upper surface — Red-purple, nearest to RHS 68B; lower one-third portion of the sepal is yellow-green, in between RHS 145C and 150C. Color when opening, lower surface — Red-purple, in between RHS 68B and 68C; lower one-third portion of the sepal is yellow-green, in between RHS 145C and 150C. Color when fully opened, upper surface — Red-purple, nearest to RHS 68B; lower one-third portion of the sepal is yellow-green, in between RHS 145C and 150C. Color when fully opened, lower surface — Red-purple, in between RHS 68B and 68C; lower one-third portion of the sepal is yellow-green, in between RHS 145C and 150C.

*Pedicels.*—Flowers are sessile.

Bract:

*Quantity.*—A prominent conduplicate bract envelopes each flower bud.

*Shape.*—Ovate.

*Length.*—4.4 cm.

*Horizontal width.*—0.7 cm.

*Vertical width.*—1.3 cm.

*Apex.*—Acute.

*Base.*—Broad Cuneate.

*Margins.*—Entire; distal 0.7 cm portion of the bract is fused.

*Color, inner surface.*—Yellow-green, nearest to RHS 145C, and fading to red-purple towards the apex, nearest to in between RHS N74C and N74D.

*Color, outer surface.*—Red-purple, nearest to RHS N74A, and slightly darker towards the apex, nearest to RHS 71C; fading to yellow-green towards the base, nearest to in between RHS 144C and 145A.

Reproductive organs:

*Androecium.*—Stamen quantity — 6. Anther — Anther shape — Linear. Anther size — 0.6 cm long and 0.1 mm wide. Anther color — Yellow-green, nearest to RHS 147D. Filament — Length — 2.1 cm. Color — White, nearest to RHS NN155C, and suffused with yellow-green towards the distal end, nearest to RHS 150D. Pollen — Amount of pollen — Moderately abundant. Pollen color — Yellow, RHS 5D.

*Gynoecium.*—Pistil quantity — One. Pistil length — 0.9 cm. Stigma — Shape — Oblong. Dimensions — 0.2 cm long and 0.1 cm in diameter. Color — Yellow-green, nearest to RHS 150D. Style — Length — 0.7 cm. Color — White, nearest to RHS 155A. Ovary — Color — Yellow-green, RHS 145C.

Seed and fruit: Not observed.

COMPARISONS WITH THE PARENT PLANTS

Plants of the new cultivar 'T1072' differ from the unnamed *Tillandsia* seed parent (not patented), by the characteristics described in Table 1.

TABLE 1

| Characteristic | 'T1072' | Seed parent. |
|---|---|---|
| Plant size. | Smaller than the pollen parent. | Larger than 'T1072'. |
| Inflorescence size, relative to plant size. | Larger than the seed parent. | Smaller than 'T1072'. |
| General coloration of the bracts. | Vibrant red-purple. | Less vibrant red-purple. |

Plants of the new cultivar 'T1072' differ from the unnamed *Tillandsia* pollen parent (not patented), by the characteristics described in Table 2.

TABLE 1

| Characteristic | 'T1072' | Pollen parent. |
|---|---|---|
| Plant size. | Smaller than the pollen parent. | Larger than 'T1072'. |
| Inflorescence size, relative to plant size. | Larger than the seed parent. | Smaller than 'T1072'. |
| General coloration of the bracts. | Vibrant red-purple. | Less vibrant red-purple. |

COMPARISON WITH THE MOST SIMILAR *TILLANDSIA* CULTIVAR KNOWN TO THE INVENTOR

'T1072' is similar to the commercial variety *Tillandsia* 'Anita' (not patented) in many horticultural characteristics. However, 'T1072' differs from 'Anita' in the following characteristics described in Table 3.

TABLE 3

| Characteristic | 'T1072' | 'Anita'. |
|---|---|---|
| Plant size. | Smaller than the pollen parent. | Larger than 'T1072'. |

TABLE 3-continued

| Characteristic | 'T1072' | 'Anita'. |
|---|---|---|
| Inflorescence size, relative to plant size. | Larger than the seed parent. | Smaller than 'T1072'. |
| General coloration of the bracts. | Vibrant red-purple. | Less vibrant red-purple. |

That which is claimed is:

1. A new and distinct variety of *Tillandsia* plant named 'T1072', substantially as described and illustrated herein.

* * * * *